(12) United States Patent
Liu et al.

(10) Patent No.: US 8,454,969 B2
(45) Date of Patent: Jun. 4, 2013

(54) SOLUBLE TUMOR NECROSIS FACTOR RECEPTOR MUTANT

(75) Inventors: Yanjun Liu, Shanghai (CN); Tong Yang, Shanghai (CN); Yijun Shen, Shanghai (CN); Jinsong Wu, Shanghai (CN); Fang Wu, Shanghai (CN)

(73) Assignees: Shanghai Fudan-Zhangjiang Bio-Pharmaceutical Co., Ltd., Shanghai (CN); Taizhou Fudan-Zhangjiang Pharmaceutical Co., Ltd., Jiangsu (CN)

( * ) Notice: Subject to any disclaimer, the term of this patent is extended or adjusted under 35 U.S.C. 154(b) by 82 days.

(21) Appl. No.: 12/745,724

(22) PCT Filed: Jan. 12, 2009

(86) PCT No.: PCT/CN2009/000037
§ 371 (c)(1),
(2), (4) Date: Jan. 31, 2011

(87) PCT Pub. No.: WO2009/143689
PCT Pub. Date: Dec. 3, 2009

(65) Prior Publication Data
US 2011/0117082 A1    May 19, 2011

(30) Foreign Application Priority Data
May 30, 2008    (CN) .......................... 2008 1 0038410

(51) Int. Cl.
*A61K 39/00*    (2006.01)

(52) U.S. Cl.
USPC ...................................... 424/192.1; 514/16.6

(58) Field of Classification Search
None
See application file for complete search history.

(56) References Cited

U.S. PATENT DOCUMENTS
2004/0170975 A1    9/2004  Savitzky et al.

FOREIGN PATENT DOCUMENTS
| CN | 1502632 A | 6/2004 |
| CN | 101003575 A | 7/2007 |
| CN | 101085813 A | 12/2007 |

OTHER PUBLICATIONS

Yang, Tong, et al., *A Variant of TNFR2-Fc Fusion Protein Exhibits Improved Efficacy in Treating Experimental Rheumatoid Arthritis* (Feb. 2010), vol. 6, Issue 2, e1000669, pp. 1-7, PLoS Computational Biology.

*Primary Examiner* — Zachary Skelding
(74) *Attorney, Agent, or Firm* — Novak Druce Connolly Bove + Quigg LLP

(57) ABSTRACT

A soluble tumor necrosis factor receptor 2 (TNFRII) mutant has an amino acid substitution at position 92Glu compared with the wild TNFRII. The mutant improves the cytotoxicity capacity of neutralizing TNFalpha and lymphotoxin. The mutant and fusion protein comprising it are useful for the treatment of TNFalpha and lymphotoxin related diseases.

20 Claims, 6 Drawing Sheets

SEQUENCE LISTING

<160> NUMBER OF SEQ ID NOS: 31

<210> SEQ ID NO 1
<211> LENGTH: 257
<212> TYPE: PRT
<213> ORGANISM: Homo sapiens

<400> SEQUENCE: 1

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp

<210> SEQ ID NO 2
<211> LENGTH: 257
<212> TYPE: PRT
<213> ORGANISM: Homo sapiens
<220> FEATURE:
<221> NAME/KEY: Mutant
<222> LOCATION: (92)..(92)

<400> SEQUENCE: 2

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln

```
            35                  40                  45
Thr Ala Gln Met Cys Cys Ser Lys Cys Ser Pro Gly Gln His Ala Lys
 50                  55                  60

Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro His Cys Leu Ser Cys
                 85                  90                  95

Gly Ser Arg Cys Ser Ser Asp Gln Val Glu Thr Gln Ala Cys Thr Arg
                100                 105                 110

Glu Gln Asn Arg Ile Cys Thr Cys Arg Pro Gly Trp Tyr Cys Ala Leu
                115                 120                 125

Ser Lys Gln Glu Gly Cys Arg Leu Cys Ala Pro Leu Arg Lys Cys Arg
130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
                180                 185                 190

Asn Ala Ser Met Asp Ala Val Cys Thr Ser Thr Ser Pro Thr Arg Ser
                195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly Asp
                245                 250                 255

Asp

<210> SEQ ID NO 3
<211> LENGTH: 257
<212> TYPE: PRT
<213> ORGANISM: Homo sapiens
<220> FEATURE:
<221> NAME/KEY: Mutant
<222> LOCATION: (92)..(92)

<400> SEQUENCE: 3

Met Ala Pro Val Ala Val Trp Ala Ala Leu Ala Val Gly Leu Glu Leu
 1               5                  10                  15

Trp Ala Ala Ala His Ala Leu Pro Ala Gln Val Ala Phe Thr Pro Tyr
                 20                  25                  30

Ala Pro Glu Pro Gly Ser Thr Cys Arg Leu Arg Glu Tyr Tyr Asp Gln
                 35                  40                  45

Thr Ala Gln Met Cys Cys Ser Lys Cys Ser Pro Gly Gln His Ala Lys
 50                  55                  60

Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro Ala Cys Leu Ser Cys
                 85                  90                  95

Gly Ser Arg Cys Ser Ser Asp Gln Val Glu Thr Gln Ala Cys Thr Arg
                100                 105                 110

Glu Gln Asn Arg Ile Cys Thr Cys Arg Pro Gly Trp Tyr Cys Ala Leu
                115                 120                 125

Ser Lys Gln Glu Gly Cys Arg Leu Cys Ala Pro Leu Arg Lys Cys Arg
130                 135                 140
```

```
Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp

<210> SEQ ID NO 4
<211> LENGTH: 257
<212> TYPE: PRT
<213> ORGANISM: Homo sapiens
<220> FEATURE:
<221> NAME/KEY: Mutant
<222> LOCATION: (92)..(92)

<400> SEQUENCE: 4

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Asn Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240
```

Phe Leu Leu Pro Met Gly Pro Ser Pro Pro Ala Glu Gly Ser Thr Gly
                    245                 250                 255

Asp

<210> SEQ ID NO 5
<211> LENGTH: 257
<212> TYPE: PRT
<213> ORGANISM: Homo sapiens
<220> FEATURE:
<221> NAME/KEY: Mutant
<222> LOCATION: (92)..(92)

<400> SEQUENCE: 5

Met Ala Pro Val Ala Val Trp Ala Ala Leu Ala Val Gly Leu Glu Leu
1               5                   10                  15

Trp Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Ser Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp

<210> SEQ ID NO 6
<211> LENGTH: 257
<212> TYPE: PRT
<213> ORGANISM: Homo sapiens
<220> FEATURE:
<221> NAME/KEY: Mutant
<222> LOCATION: (89)..(89)
<220> FEATURE:
<221> NAME/KEY: Mutant
<222> LOCATION: (92)..(92)

<400> SEQUENCE: 6

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Tyr Val Pro Asn Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp

<210> SEQ ID NO 7
<211> LENGTH: 257
<212> TYPE: PRT
<213> ORGANISM: Homo sapiens
<220> FEATURE:
<221> NAME/KEY: Mutant
<222> LOCATION: (89)..(89)
<220> FEATURE:
<221> NAME/KEY: Mutant
<222> LOCATION: (92)..(92)

<400> SEQUENCE: 7

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Tyr Val Pro Ser Cys Leu Ser Cys
```

-continued

```
                        85                  90                  95
Gly Ser Arg Cys Ser Ser Asp Gln Val Glu Thr Gln Ala Cys Thr Arg
            100                 105                 110
Glu Gln Asn Arg Ile Cys Thr Cys Arg Pro Gly Trp Tyr Cys Ala Leu
            115                 120                 125
Ser Lys Gln Glu Gly Cys Arg Leu Cys Ala Pro Leu Arg Lys Cys Arg
            130                 135                 140
Pro Gly Phe Gly Val Ala Arg Pro Gly Thr Glu Thr Ser Asp Val Val
145                 150                 155                 160
Cys Lys Pro Cys Ala Pro Gly Thr Phe Ser Asn Thr Thr Ser Ser Thr
            165                 170                 175
Asp Ile Cys Arg Pro His Gln Ile Cys Asn Val Val Ala Ile Pro Gly
            180                 185                 190
Asn Ala Ser Met Asp Ala Val Cys Thr Ser Thr Ser Pro Thr Arg Ser
            195                 200                 205
Met Ala Pro Gly Ala Val His Leu Pro Gln Pro Val Ser Thr Arg Ser
            210                 215                 220
Gln His Thr Gln Pro Thr Pro Glu Pro Ser Thr Ala Pro Ser Thr Ser
225                 230                 235                 240
Phe Leu Leu Pro Met Gly Pro Ser Pro Ala Glu Gly Ser Thr Gly
            245                 250                 255
Asp

<210> SEQ ID NO 8
<211> LENGTH: 257
<212> TYPE: PRT
<213> ORGANISM: Homo sapiens
<220> FEATURE:
<221> NAME/KEY: Mutant
<222> LOCATION: (89)..(89)
<220> FEATURE:
<221> NAME/KEY: Mutant
<222> LOCATION: (92)..(92)

<400> SEQUENCE: 8

Met Ala Pro Val Ala Val Trp Ala Ala Leu Ala Val Gly Leu Glu Leu
1               5                   10                  15
Trp Ala Ala Ala His Ala Leu Pro Ala Gln Val Ala Phe Thr Pro Tyr
            20                  25                  30
Ala Pro Glu Pro Gly Ser Thr Cys Arg Leu Arg Glu Tyr Tyr Asp Gln
            35                  40                  45
Thr Ala Gln Met Cys Cys Ser Lys Cys Ser Pro Gly Gln His Ala Lys
            50                  55                  60
Val Phe Cys Thr Lys Thr Ser Asp Thr Val Cys Asp Ser Cys Glu Asp
65                  70                  75                  80
Ser Thr Tyr Thr Gln Leu Trp Asn Phe Val Pro Asn Cys Leu Ser Cys
            85                  90                  95
Gly Ser Arg Cys Ser Ser Asp Gln Val Glu Thr Gln Ala Cys Thr Arg
            100                 105                 110
Glu Gln Asn Arg Ile Cys Thr Cys Arg Pro Gly Trp Tyr Cys Ala Leu
            115                 120                 125
Ser Lys Gln Glu Gly Cys Arg Leu Cys Ala Pro Leu Arg Lys Cys Arg
            130                 135                 140
Pro Gly Phe Gly Val Ala Arg Pro Gly Thr Glu Thr Ser Asp Val Val
145                 150                 155                 160
Cys Lys Pro Cys Ala Pro Gly Thr Phe Ser Asn Thr Thr Ser Ser Thr
            165                 170                 175
```

```
Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp
```

<210> SEQ ID NO 9
<211> LENGTH: 489
<212> TYPE: PRT
<213> ORGANISM: Artificial Sequence
<220> FEATURE:
<223> OTHER INFORMATION: Fusion protein of the TNFRp75 mutant and the Fc
      fragment

<400> SEQUENCE: 9

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro His Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Glu Pro Lys Ser Cys Asp Lys Thr His Thr Cys Pro Pro Cys Pro
            260                 265                 270
```

-continued

```
Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
        340                 345                 350

Gln Asp Trp Leu Asn Gly Lys Glu Tyr Lys Cys Lys Val Ser Asn Lys
    355                 360                 365

Ala Leu Pro Ala Pro Ile Glu Lys Thr Ile Ser Lys Ala Lys Gly Gln
370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
            405                 410                 415

Ser Asp Ile Ala Val Glu Trp Glu Ser Asn Gly Gln Pro Glu Asn Asn
        420                 425                 430

Tyr Lys Thr Thr Pro Pro Val Leu Asp Ser Asp Gly Ser Phe Phe Leu
    435                 440                 445

Tyr Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
            485

<210> SEQ ID NO 10
<211> LENGTH: 489
<212> TYPE: PRT
<213> ORGANISM: Artificial Sequence
<220> FEATURE:
<223> OTHER INFORMATION: Fusion protein of the TNFRp75 mutant and the Fc
      fragment

<400> SEQUENCE: 10

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Ala Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140
```

```
Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
            165                 170                 175

Asp Ile Cys Arg Pro His Gln Ile Cys Asn Val Val Ala Ile Pro Gly
        180                 185                 190

Asn Ala Ser Met Asp Ala Val Cys Thr Ser Thr Ser Pro Thr Arg Ser
    195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
            275                 280                 285

Pro Lys Asp Thr Leu Met Ile Ser Arg Thr Pro Glu Val Thr Cys Val
290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
            355                 360                 365

Ala Leu Pro Ala Pro Ile Glu Lys Thr Ile Ser Lys Ala Lys Gly Gln
        370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 11
<211> LENGTH: 489
<212> TYPE: PRT
<213> ORGANISM: Artificial Sequence
<220> FEATURE:
<223> OTHER INFORMATION: Fusion protein of the TNFRp75 mutant and the Fc
      fragment

<400> SEQUENCE: 11

Met Ala Pro Val Ala Val Trp Ala Ala Leu Ala Val Gly Leu Glu Leu
1               5                   10                  15
```

-continued

```
Trp Ala Ala Ala His Ala Leu Pro Ala Gln Val Ala Phe Thr Pro Tyr
         20                  25                  30
Ala Pro Glu Pro Gly Ser Thr Cys Arg Leu Arg Glu Tyr Tyr Asp Gln
         35                  40                  45
Thr Ala Gln Met Cys Cys Ser Lys Cys Ser Pro Gly Gln His Ala Lys
 50                  55                  60
Val Phe Cys Thr Lys Thr Ser Asp Thr Val Cys Asp Ser Cys Glu Asp
 65                  70                  75                  80
Ser Thr Tyr Thr Gln Leu Trp Asn Trp Val Pro Asn Cys Leu Ser Cys
             85                  90                  95
Gly Ser Arg Cys Ser Ser Asp Gln Val Glu Thr Gln Ala Cys Thr Arg
        100                 105                 110
Glu Gln Asn Arg Ile Cys Thr Cys Arg Pro Gly Trp Tyr Cys Ala Leu
        115                 120                 125
Ser Lys Gln Glu Gly Cys Arg Leu Cys Ala Pro Leu Arg Lys Cys Arg
        130                 135                 140
Pro Gly Phe Gly Val Ala Arg Pro Gly Thr Glu Thr Ser Asp Val Val
145                 150                 155                 160
Cys Lys Pro Cys Ala Pro Gly Thr Phe Ser Asn Thr Thr Ser Ser Thr
                165                 170                 175
Asp Ile Cys Arg Pro His Gln Ile Cys Asn Val Val Ala Ile Pro Gly
            180                 185                 190
Asn Ala Ser Met Asp Ala Val Cys Thr Ser Thr Ser Pro Thr Arg Ser
            195                 200                 205
Met Ala Pro Gly Ala Val His Leu Pro Gln Pro Val Ser Thr Arg Ser
210                 215                 220
Gln His Thr Gln Pro Thr Pro Glu Pro Ser Thr Ala Pro Ser Thr Ser
225                 230                 235                 240
Phe Leu Leu Pro Met Gly Pro Ser Pro Ala Glu Gly Ser Thr Gly
                245                 250                 255
Asp Glu Pro Lys Ser Cys Asp Lys Thr His Thr Cys Pro Pro Cys Pro
            260                 265                 270
Ala Pro Glu Leu Leu Gly Gly Pro Ser Val Phe Leu Phe Pro Pro Lys
            275                 280                 285
Pro Lys Asp Thr Leu Met Ile Ser Arg Thr Pro Glu Val Thr Cys Val
        290                 295                 300
Val Val Asp Val Ser His Glu Asp Pro Glu Val Lys Phe Asn Trp Tyr
305                 310                 315                 320
Val Asp Gly Val Glu Val His Asn Ala Lys Thr Lys Pro Arg Glu Glu
                325                 330                 335
Gln Tyr Asn Ser Thr Tyr Arg Val Val Ser Val Leu Thr Val Leu His
            340                 345                 350
Gln Asp Trp Leu Asn Gly Lys Glu Tyr Lys Cys Lys Val Ser Asn Lys
            355                 360                 365
Ala Leu Pro Ala Pro Ile Glu Lys Thr Ile Ser Lys Ala Lys Gly Gln
        370                 375                 380
Pro Arg Glu Pro Gln Val Tyr Thr Leu Pro Pro Ser Arg Asp Glu Leu
385                 390                 395                 400
Thr Lys Asn Gln Val Ser Leu Thr Cys Leu Val Lys Gly Phe Tyr Pro
                405                 410                 415
Ser Asp Ile Ala Val Glu Trp Glu Ser Asn Gly Gln Pro Glu Asn Asn
            420                 425                 430
Tyr Lys Thr Thr Pro Pro Val Leu Asp Ser Asp Gly Ser Phe Phe Leu
        435                 440                 445
```

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 12
<211> LENGTH: 489
<212> TYPE: PRT
<213> ORGANISM: Artificial Sequence
<220> FEATURE:
<223> OTHER INFORMATION: Fusion protein of the TNFRp75 mutant and the Fc
      fragment

<400> SEQUENCE: 12

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Ser Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

```
Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
            355                 360                 365

Ala Leu Pro Ala Pro Ile Glu Lys Thr Ile Ser Lys Ala Lys Gly Gln
        370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
            435                 440                 445

Tyr Ser Lys Leu Thr Val Asp Lys Ser Arg Trp Gln Gln Gly Asn Val
        450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 13
<211> LENGTH: 489
<212> TYPE: PRT
<213> ORGANISM: Artificial Sequence
<220> FEATURE:
<223> OTHER INFORMATION: protein of the TNFRp75 mutant and the Fc
      fragment

<400> SEQUENCE: 13

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Tyr Val Pro Asn Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190
```

Asn Ala Ser Met Asp Ala Val Cys Thr Ser Thr Ser Pro Thr Arg Ser
            195                 200                 205

Met Ala Pro Gly Ala Val His Leu Pro Gln Pro Val Ser Thr Arg Ser
            210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
            245                 250                 255

Asp Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
            275                 280                 285

Pro Lys Asp Thr Leu Met Ile Ser Arg Thr Pro Glu Val Thr Cys Val
            290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
            325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
            355                 360                 365

Ala Leu Pro Ala Pro Ile Glu Lys Thr Ile Ser Lys Ala Lys Gly Gln
            370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
            405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
            435                 440                 445

Tyr Ser Lys Leu Thr Val Asp Lys Ser Arg Trp Gln Gln Gly Asn Val
450                 455                 460

Phe Ser Cys Ser Val Met His Glu Ala Leu His Asn His Tyr Thr Gln
465                 470                 475                 480

Lys Ser Leu Ser Leu Ser Pro Gly Lys
            485

<210> SEQ ID NO 14
<211> LENGTH: 489
<212> TYPE: PRT
<213> ORGANISM: Artificial Sequence
<220> FEATURE:
<223> OTHER INFORMATION: Fusion protein of the TNFRp75 mutant and the Fc
      fragment

<400> SEQUENCE: 14

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

```
Val Phe Cys Thr Lys Thr Ser Asp Thr Val Cys Asp Ser Cys Glu Asp
 65                  70                  75                  80

Ser Thr Tyr Thr Gln Leu Trp Asn Tyr Val Pro Ser Cys Leu Ser Cys
                 85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
            130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
            195                 200                 205

Met Ala Pro Gly Ala Val His Leu Pro Gln Pro Val Ser Thr Arg Ser
210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
            275                 280                 285

Pro Lys Asp Thr Leu Met Ile Ser Arg Thr Pro Glu Val Thr Cys Val
            290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys
            355                 360                 365

Ala Leu Pro Ala Pro Ile Glu Lys Thr Ile Ser Lys Ala Lys Gly Gln
            370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
            435                 440                 445

Tyr Ser Lys Leu Thr Val Asp Lys Ser Arg Trp Gln Gln Gly Asn Val
            450                 455                 460

Phe Ser Cys Ser Val Met His Glu Ala Leu His Asn His Tyr Thr Gln
465                 470                 475                 480

Lys Ser Leu Ser Leu Ser Pro Gly Lys
```

-continued

485

<210> SEQ ID NO 15
<211> LENGTH: 489
<212> TYPE: PRT
<213> ORGANISM: Artificial Sequence
<220> FEATURE:
<223> OTHER INFORMATION: Fusion protein of the TNFRp75 mutant and the Fc
fragment

<400> SEQUENCE: 15

Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Phe Val Pro Asn Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Pro Ala Glu Gly Ser Thr Gly
                245                 250                 255

Asp Glu Pro Lys Ser Cys Asp Lys Thr His Thr Cys Pro Pro Cys Pro
            260                 265                 270

Ala Pro Glu Leu Leu Gly Gly Pro Ser Val Phe Leu Phe Pro Pro Lys
        275                 280                 285

Pro Lys Asp Thr Leu Met Ile Ser Arg Thr Pro Glu Val Thr Cys Val
    290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
            340                 345                 350

Gln Asp Trp Leu Asn Gly Lys Glu Tyr Lys Cys Lys Val Ser Asn Lys

```
                355                 360                 365
Ala Leu Pro Ala Pro Ile Glu Lys Thr Ile Ser Lys Ala Lys Gly Gln
        370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
            420                 425                 430

Tyr Lys Thr Thr Pro Pro Val Leu Asp Ser Asp Gly Ser Phe Phe Leu
        435                 440                 445

Tyr Ser Lys Leu Thr Val Asp Lys Ser Arg Trp Gln Gln Gly Asn Val
    450                 455                 460

Phe Ser Cys Ser Val Met His Glu Ala Leu His Asn His Tyr Thr Gln
465                 470                 475                 480

Lys Ser Leu Ser Leu Ser Pro Gly Lys
                485

<210> SEQ ID NO 16
<211> LENGTH: 28
<212> TYPE: DNA
<213> ORGANISM: Artificial Sequence
<220> FEATURE:
<223> OTHER INFORMATION: DNA primer

<400> SEQUENCE: 16
aagcttatgg ctcccgtcgc cgtctggg                                          28

<210> SEQ ID NO 17
<211> LENGTH: 20
<212> TYPE: DNA
<213> ORGANISM: Artificial Sequence
<220> FEATURE:
<223> OTHER INFORMATION: DNA primer

<400> SEQUENCE: 17
tgcttgagct gtggctcccg                                                   20

<210> SEQ ID NO 18
<211> LENGTH: 26
<212> TYPE: DNA
<213> ORGANISM: Artificial Sequence
<220> FEATURE:
<223> OTHER INFORMATION: DNA primer

<400> SEQUENCE: 18
gaattcctat ttacccggag acaggg                                            26

<210> SEQ ID NO 19
<211> LENGTH: 28
<212> TYPE: DNA
<213> ORGANISM: Artificial Sequence
<220> FEATURE:
<223> OTHER INFORMATION: DNA primer

<400> SEQUENCE: 19
cgggagccac agctcaagca gtggggaa                                          28

<210> SEQ ID NO 20
<211> LENGTH: 20
<212> TYPE: DNA
<213> ORGANISM: Artificial Sequence
<220> FEATURE:
```

<223> OTHER INFORMATION: DNA primer

<400> SEQUENCE: 20
tgcttgagct gtggctcccg                                           20

<210> SEQ ID NO 21
<211> LENGTH: 28
<212> TYPE: DNA
<213> ORGANISM: Artificial Sequence
<220> FEATURE:
<223> OTHER INFORMATION: DNA primer

<400> SEQUENCE: 21
cgggagccac agctcaagca ggcgggaa                                  28

<210> SEQ ID NO 22
<211> LENGTH: 20
<212> TYPE: DNA
<213> ORGANISM: Artificial Sequence
<220> FEATURE:
<223> OTHER INFORMATION: DNA primer

<400> SEQUENCE: 22
tgcttgagct gtggctcccg                                           20

<210> SEQ ID NO 23
<211> LENGTH: 28
<212> TYPE: DNA
<213> ORGANISM: Artificial Sequence
<220> FEATURE:
<223> OTHER INFORMATION: DNA primer

<400> SEQUENCE: 23
cgggagccac agctcaagca gttgggaa                                  28

<210> SEQ ID NO 24
<211> LENGTH: 20
<212> TYPE: DNA
<213> ORGANISM: Artificial Sequence
<220> FEATURE:
<223> OTHER INFORMATION: DNA primer

<400> SEQUENCE: 24
tgcttgagct gtggctcccg                                           20

<210> SEQ ID NO 25
<211> LENGTH: 28
<212> TYPE: DNA
<213> ORGANISM: Artificial Sequence
<220> FEATURE:
<223> OTHER INFORMATION: DNA Primer

<400> SEQUENCE: 25
cgggagccac agctcaagca gctgggaa                                  28

<210> SEQ ID NO 26
<211> LENGTH: 17
<212> TYPE: DNA
<213> ORGANISM: Artificial Sequence
<220> FEATURE:
<223> OTHER INFORMATION: DNA primer

<400> SEQUENCE: 26
gttcccgagt gcttgag                                              17

<210> SEQ ID NO 27

```
<211> LENGTH: 53
<212> TYPE: DNA
<213> ORGANISM: Artificial Sequence
<220> FEATURE:
<223> OTHER INFORMATION: DNA primer

<400> SEQUENCE: 27
cgggagccac agctcaagca gttgggaacg tagttccaga gctgggtgta tgt        53

<210> SEQ ID NO 28
<211> LENGTH: 17
<212> TYPE: DNA
<213> ORGANISM: Artificial Sequence
<220> FEATURE:
<223> OTHER INFORMATION: DNA primer

<400> SEQUENCE: 28
gttcccgagt gcttgag                                                17

<210> SEQ ID NO 29
<211> LENGTH: 53
<212> TYPE: DNA
<213> ORGANISM: Artificial Sequence
<220> FEATURE:
<223> OTHER INFORMATION: DNA primer

<400> SEQUENCE: 29
cgggagccac agctcaagca gctgggaacg tagttccaga gctgggtgta tgt        53

<210> SEQ ID NO 30
<211> LENGTH: 17
<212> TYPE: DNA
<213> ORGANISM: Artificial Sequence
<220> FEATURE:
<223> OTHER INFORMATION: DNA primer

<400> SEQUENCE: 30
gttcccgagt gcttgag                                                17

<210> SEQ ID NO 31
<211> LENGTH: 53
<212> TYPE: DNA
<213> ORGANISM: Artificial Sequence
<220> FEATURE:
<223> OTHER INFORMATION: DNA primer

<400> SEQUENCE: 31
cgggagccac agctcaagca gttgggaacg aagttccaga gctgggtgta tgt        53
```

SOLUBLE TUMOR NECROSIS FACTOR RECEPTOR MUTANT

CROSS-REFERENCE TO RELATED APPLICATIONS

This is the U.S. national phase of International Application No. PCT/CN2009/000037, filed Jan. 12, 2009, which claims the benefit of Chinese Patent Application No. 200810038410.X, filed May 30, 2008.

TECHNICAL FIELD

The present invention is in the field of biopharmaceuticals, and more particularly, it relates to derivatives of the tumor necrosis factor (TNF) receptor and use thereof in pharmaceuticals.

BACKGROUND OF THE INVENTION

The tumor necrosis factor α (TNFα) a member of the tumor necrosis factor superfamily, has biological activities of modulating immunological response, cell apoptosis, cell differentiation, and the like. TNFα has two intracellular receptors, TNF receptor 1 (TNFRp55) and TNF receptor 2 (TNFRp75). Overproduction of TNFα is an underlying mechanism of autoimmune diseases such as rheumatoid arthritis. Blocking excess TNFa by its antagonists including soluble TNFRp75:Fc fusion proteins such as Etanercept and anti-TNF monoclonal antibodies such as Infliximab has been validated as an effective treatment for rheumatoid arthritis.

Etanercept can bind both TNFα and lymphotoxin (LT), but it requires a relatively large clinical dose at about 25-50 mg, which tends to cause erythema when administered via subcutaneous injection. Therefore, it is highly demanded to develop a TNFRp75 which can bind TNF and lymphotoxin with high affinity, and in turn to develop a TNFRp75:Fc fusion protein as an antibody drug.

SUMMARY OF THE INVENTION

One of the objectives of the present invention is to provide a soluble receptor having a high neutralizing activity to TNFα and/or lymphotoxin, thereby reducing dose of the soluble receptor required for neutralizing TNFα, improving therapeutic effect on autoimmune diseases and decreasing production cost of the drug.

Another objective of the present invention is to provide a fusion protein formed between a soluble receptor having a higher neutralizing activity and an additional amino acid fragment.

Still another objective of the present invention is to provide a DNA sequence encoding the soluble receptor or the fusion protein stated above.

Still another objective of the present invention is to provide use of a soluble receptor having a higher neutralizing activity to TNFα and/or lymphotoxin or a fusion protein thereof in pharmaceuticals.

Still another objective of the present invention is to provide a pharmaceutical composition comprising the soluble receptor or a fusion protein thereof stated above.

Inventors of the present invention have made intensive studies on the structures of TNF receptor 2, TNFα and LT through molecular structure modeling and found that the amino acid at position 92 of the TNF receptor 2 is essential for its binding with TNFα and LT. Then, the inventors made a rational point mutation at the amino acid position 92 and obtained a soluble mutant of TNF receptor 2, which has a high neutralizing activity to TNFα and lymphotoxin.

In the first aspect, the present invention discloses a soluble TNFRp75 mutant that has an amino acid substitution at the amino acid position 92 of the wild-type sequence (SEQ ID NO. 1). The neutralizing activity of the soluble TNFRp75 mutant against the cytotoxicity of TNFα and lymphotoxin is increased by above 30% when compared with the wild type.

In a preferred embodiment, the glutamic acid residue (E) at the amino acid position 92 is substituted by one of Asn, His, Ser, Ala, Lys or Gln. That is, the amino acid E at position 92 of the sequence set forth in SEQ ID NO. 1 is substituted by N, H, S, A, K or Q, respectively. The exemplary examples are as follows.

The amino acid sequence of TNFRp75 (E92H) mutant is set forth in SEQ ID NO. 2, wherein the position 92 is Histidine (His), and the N-terminal amino acid residues 1-22 are a signal peptide.

The amino acid sequence of TNFRp75 (E92A) mutant is set forth in SEQ ID NO. 3, wherein the position 92 is Alanine (Ala), and the N-terminal amino acid residues 1-22 are a signal peptide.

The amino acid sequence of TNFRp75 (E92N) mutant is set forth in SEQ ID NO. 4, wherein the position 92 is Asparagine (Asn), and the N-terminal amino acid residues 1-22 are a signal peptide.

The amino acid sequence of TNFRp75 (E92S) mutant is set forth in SEQ ID NO. 5, wherein the position 92 is Serine (Ser), and the N-terminal amino acid residues 1-22 are a signal peptide.

In some preferred embodiments, the Tryptophan (Trp) at position 89 is further substituted by Tyr, Phe, His, Lys, Met or Leu, in addition to the substitution of Glu (E) at position 92. The exemplary examples are as follows.

The amino acid sequence of TNFRp75 (E92N, W89Y) mutant is set forth in SEQ ID NO. 6, wherein the position 89 is Tyrosine (Tyr), position 92 is Asparagine (Asn), and the N-terminal amino acid residues 1-22 are a signal peptide.

The amino acid sequence of TNFRp75 (E92S, W89Y) mutant is set forth in SEQ ID NO. 7, wherein the position 89 is Tyrosine (Tyr), position 92 is Serine (Ser), and the N-terminal amino acid residues 1-22 are a signal peptide.

The amino acid sequence of TNFRp75 (E92N, W89F) mutant is set forth in SEQ ID NO. 8, wherein the position 89 is Phenylalanine (Phe), position 92 is Asparagine (Asn), and the N-terminal amino acid residues 1-22 are a signal peptide.

In the second aspect, the present invention discloses a fusion protein comprising a soluble TNFRp75 mutant and an additional amino acid fragment. Said additional amino acid fragment acts to enhance the stability and improve the biological half-life of the TNFRp75 mutant.

Said additional amino acid fragment is selected from the group consisting of the human immunoglobulin (IgG) constant region (Fc) and one of the five functional regions of Albumin.

Said additional amino acid fragment is at the C-terminus of the TNFRp75 mutant.

In a preferred embodiment, said additional amino acid fragment is the 232 amino acid residues of human immunoglobulin (IgG) constant region (Fc). A fusion protein is formed by the soluble TNFRp75 mutant and the 232 amino acids of the Fc fragment at the C-terminus of human IgG, with or without an additional connecting fragment between the two components, preferably without an additional connecting fragment. The exemplary examples are as follows:

the amino acid sequence of TNFRp75 (E92H): Fc set forth in SEQ ID NO. 9;

the amino acid sequence of TNFRp75 (E92A): Fc set forth in SEQ ID NO. 10;

the amino acid sequence of TNFRp75 (E92N): Fc set forth in SEQ ID NO. 11;

the amino acid sequence of TNFRp75 (E92S): Fc set forth in SEQ ID NO. 12;

the amino acid sequence of TNFRp75 (E92N, W89Y): Fc set forth in SEQ ID NO. 13;

the amino acid sequence of TNFRp75 (E92S, W89Y): Fc set forth in SEQ ID NO. 14;

the amino acid sequence of TNFRp75 (E92N, W89F): Fc set forth in SEQ ID NO. 15.

In the third aspect, the present invention discloses a DNA sequence encoding the soluble receptor or the fusion protein stated above. As well known in the art, the DNA sequences encoding the soluble receptors or the fusion proteins according to the present invention may vary according to codon degeneracy and codon bias of different host cells, but these DNA sequences still fall into the scope of the present invention, as long as the amino acid sequences encoded by these DNA sequences do not change.

In the fourth aspect, the present invention discloses use of the soluble TNFRp75 mutant or a fusion protein thereof stated above in pharmaceuticals, in particular, in the treatment of diseases associated with over-expression of TNFα and/or lymphotoxin, including but not limited to, rheumatoid arthritis, psoriasis, scleroderma, Sjogren's syndrome, ankylosing spondylitis, lupus erythematosus, dermatomyositis, and systemic lupus erythematosus-like syndrome.

In the fifth aspect, the present invention discloses a pharmaceutical composition comprising the soluble TNFRp75 mutant or a fusion protein thereof stated above.

The TNFRp75 mutants and the fusion proteins thereof in the present invention have an increased binding capacity to TNF and lymphotoxin. For example, the neutralizing activity of the soluble TNFRp75 (E92N): Fc to TNFα is 1.33 times that of the wild-type soluble TNFRp75: Fc (ENBREL from AMGEN), and the neutralizing activity to LT is 2.77 times that of the wild-type soluble TNFRp75: Fc (ENBREL from AMGEN). The TNFRp75 mutant and the fusion protein thereof in the present invention are useful in the treatment of diseases related to TNFα and LT. Because of the increased activity, the clinical dose could be reduced so as to decrease the probability of rising erythema when the drug is administered via subcutaneous injection. In addition, increase of the dissociation time in terms of TNFα binding will be advantageous for an extended action time of the drug.

BRIEF DESCRIPTION OF THE DRAWINGS

FIG. 1A: Neutralization of the TNFRp75 (E92A): Fc fusion protein against the cytotoxicity of TNFα.

FIG. 1B: Neutralization of the TNFRp75 (E92A): Fc fusion protein against the cytotoxicity of $LT_{28-171}$.

FIG. 2A: Neutralization of the TNFRp75 (E92H): Fc fusion protein against the cytotoxicity of TNFα.

FIG. 2B: Neutralization of the TNFRp75 (E92H): Fc fusion protein against the cytotoxicity of $LT_{28-171}$.

FIG. 3A: Neutralization of the TNFRp75 (E92N): Fc fusion protein against the cytotoxicity of TNFα.

FIG. 3B: Neutralization of the TNFRp75 (E92N): Fc fusion protein against the cytotoxicity of $LT_{28-171}$.

FIG. 4A: Neutralization of the TNFRp75 (E92N□W89Y): Fc fusion protein against the cytotoxicity of TNFα.

FIG. 4B: Neutralization of the TNFRp75 (E92N□W89Y): Fc fusion protein against the cytotoxicity of $LT_{28-171}$.

FIG. 5A: Neutralization of the TNFRp75 (E92S□W89Y): Fc fusion protein against the cytotoxicity of TNFα.

FIG. 5B: Neutralization of the TNFRp75 (E92S□W89Y): Fc fusion protein against the cytotoxicity of $LT_{28-171}$.

FIG. 6A: Neutralization of the TNFRp75 (E92N□W89F): Fc fusion protein against the cytotoxicity of TNFα.

FIG. 6B: Neutralization of the TNFRp75 (E92N□W89F): Fc fusion protein against the cytotoxicity of $LT_{28-171}$.

DETAILED DESCRIPTION OF THE INVENTION

Figure 1:
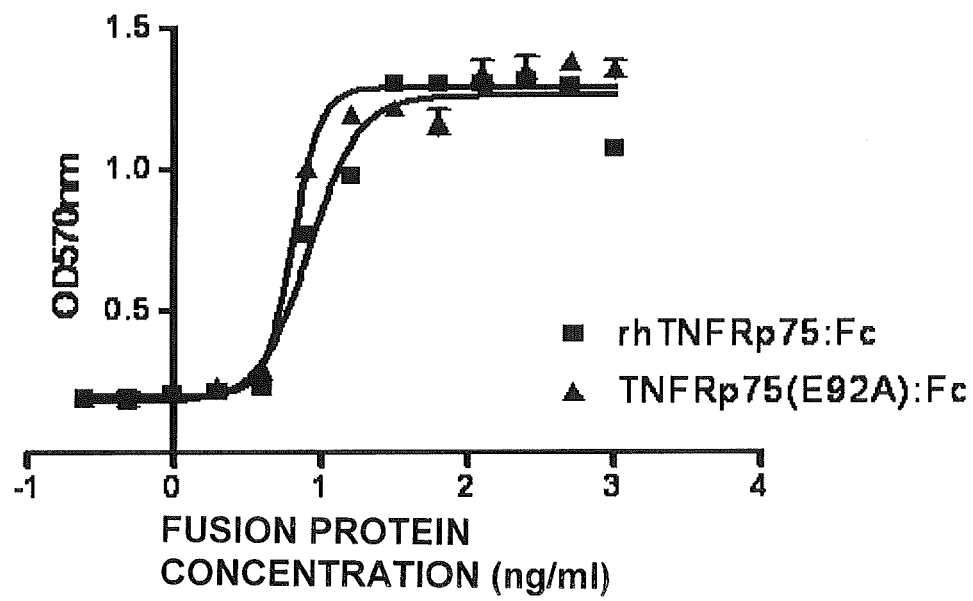
FIG. 1-6: Neutralization of the TNFRp75 mutant: Fc fusion protein against the cytotoxicity of TNFα or $LT_{28-171}$□ Lithe wild-type TNFRp75: Fc fusion protein used as control in each experiment.
Figure 1:
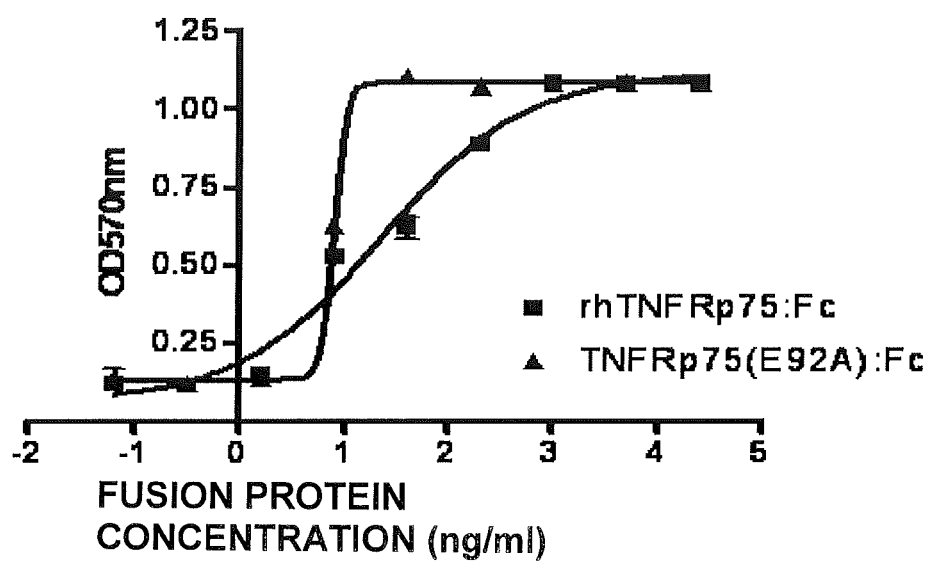
Figure 2:
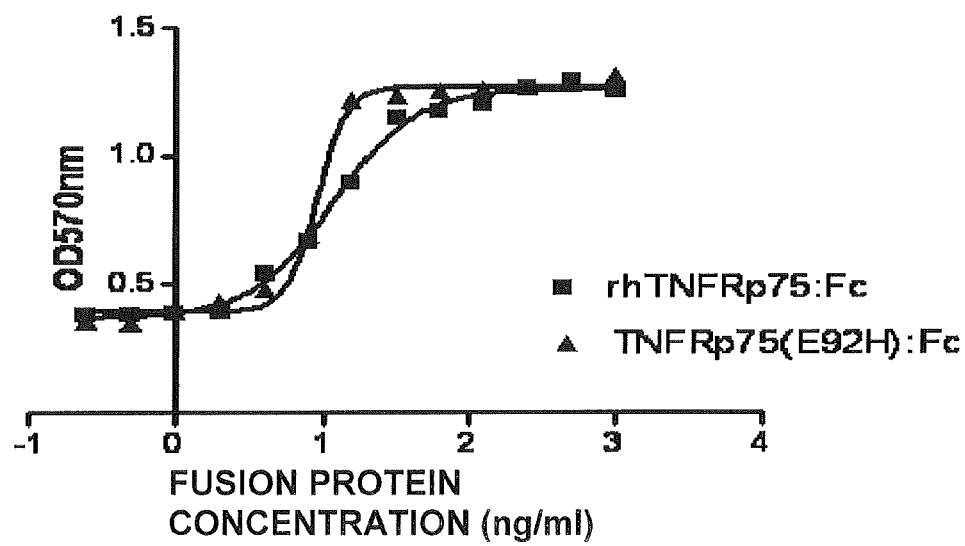
Figure 2:
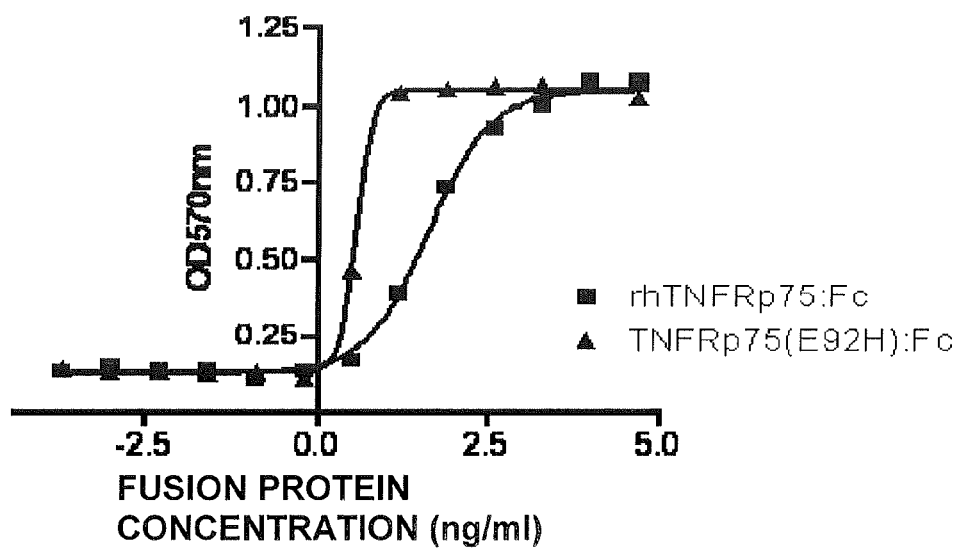
Figure 3:
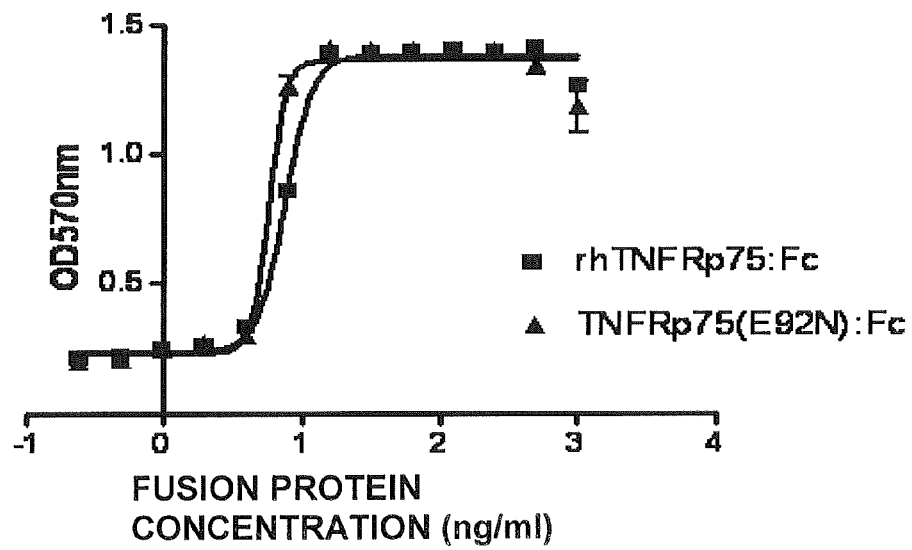
Figure 3:
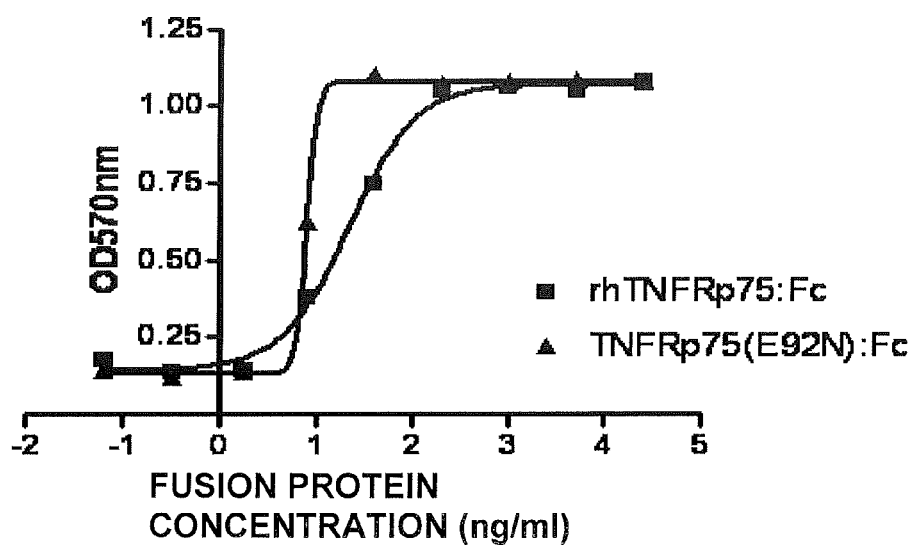
Figure 4:
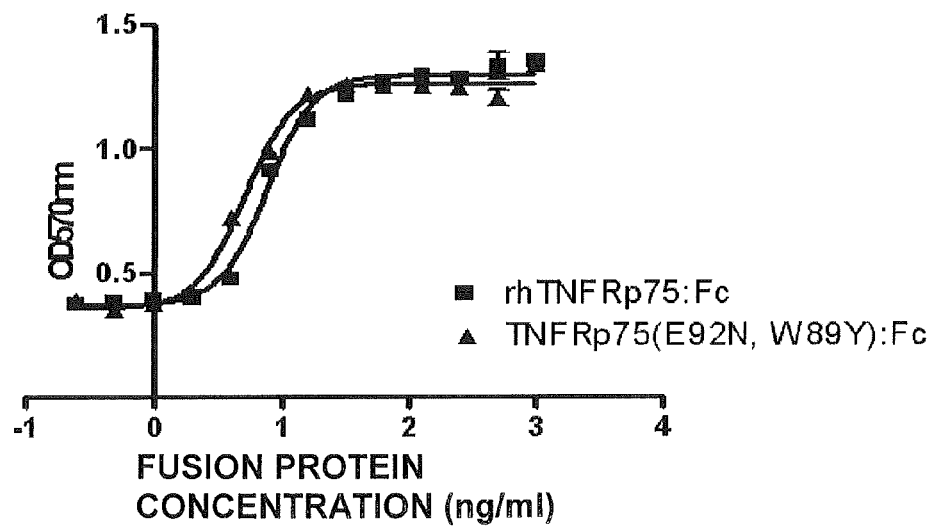
Figure 4:
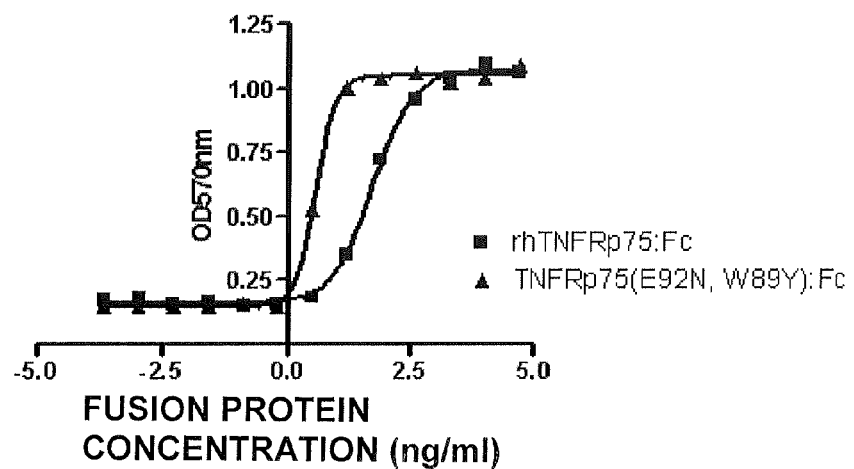
Figure 5:
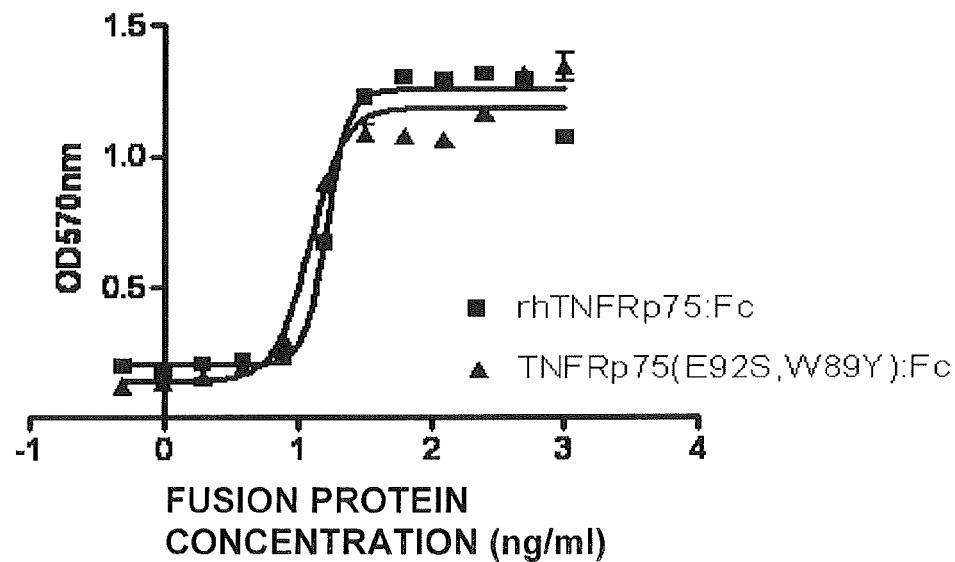
Figure 5:
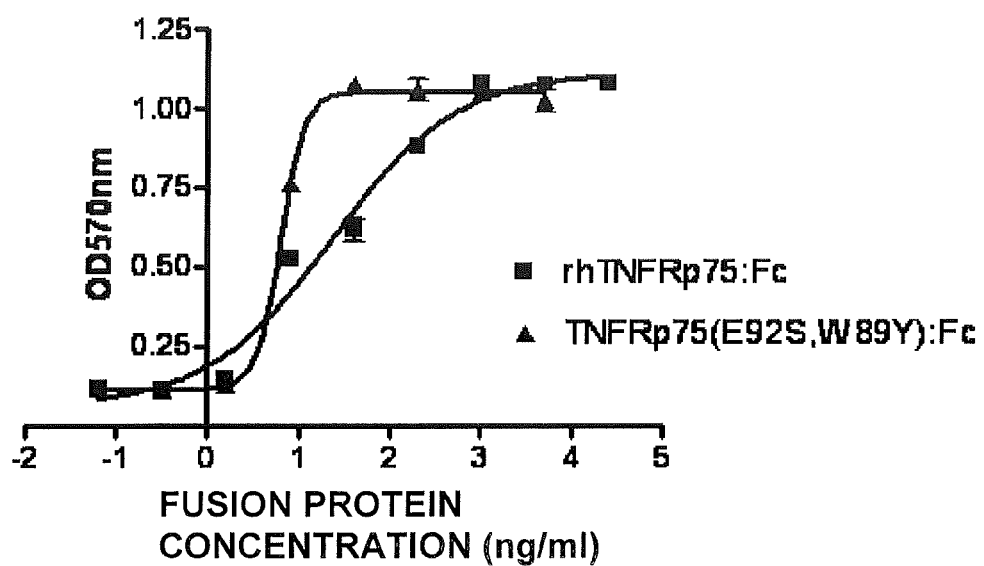
Figure 6:
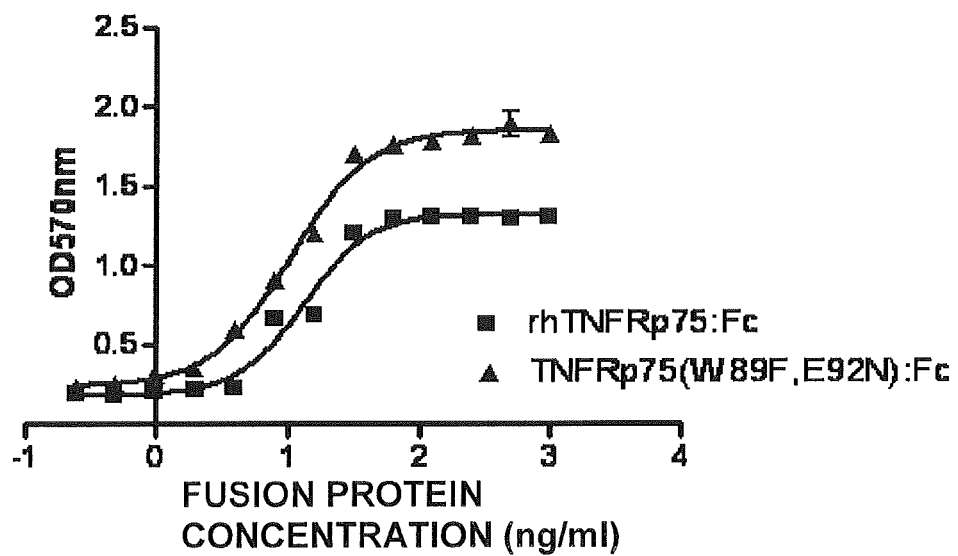
Figure 6:
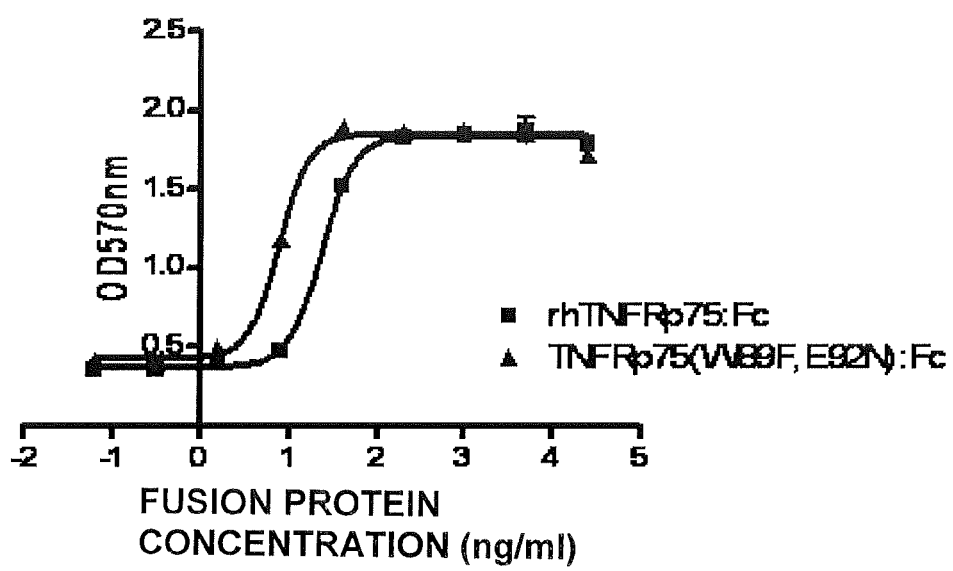

The present invention is now further illustrated with reference to the following examples. It should be understood that the examples are merely illustrative but in no way intended to limit the scope of the invention. Experiments in the following examples that do not indicate specific experimental conditions are performed under conventional conditions or conditions suggested by manufacters. Unless specifically indicated otherwise, the ratio and percentage are based on weight.

As used herein, the terms "TNF receptor 2", "TNFRp75" and "TNFRp75 receptor", which can be interchangeably used, include the TNFRp75 receptor derived from human as well as the homologues thereof derived from a mouse (or rat), pig, horse or bovine. Preferably, it is human TNFRp75 receptor. The amino acid sequence of the natural-occurring wild-type human TNFRp75 receptor is set forth in SEQ ID NO. 1.

"Soluble TNFp75 receptor", as used in the context of the present invention, refers to the extracellular region of a TNFp75 receptor, that is, the ligand-binding domain consisting of the N-terminal amino acid residues 1-257 of the wild-type human TNFp75 receptor, wherein the N-terminal amino acid residues 1-22 are a signal peptide.

"Soluble TNFp75 receptor" or "soluble TNFp75 receptor mutant in the present invention", as used in the context of the present invention, means a TNFp75 receptor mutant that has an increased binding ability to TNF, preferably by at least 2 times that of the wild-type, and has an increased binding ability to LT, preferably by at least 10 times. Such a mutant can be created by amino acid insertion, deletion or substitution, preferably by amino acid substitution. For example, E92H means that in the mutant His substitutes the Glu at position 92 of the wild-type sequence, numbering of the amino acid according to the wide-type sequence.

"Amino acid substitution" as used in the context of the present invention refers to the experimentally induced replacement of one or more amino acids in a polypeptide, protein, or fragment of a protein, with another one or several others by genetic engineering or artificial synthetic technology.

The TNFp75 mutant protein in the present invention can be created by synthesizing primers according to the human soluble TNFp75 receptor sequence already known in the art and then amplifying the encoding sequence of the soluble TNFp75 receptor by PCR method; alternatively, the encoding sequence of the soluble TNFp75 receptor can be synthesized artificially. Technologies for genetic modification of the encoding sequence of the soluble TNFp75 receptor, such as the point mutagenesis technology, are well known to those of skill in the art. See, for example, Mutagenesis: a Practical Approach", M. J. McPherson, Ed., (IRL press, Oxford, UK. (1991), which includes for example site-directed mutagenesis, cassette mutagenesis and mutagenic polymerase chain reaction (PCR).

Approaches for conjugation of the fragment encoding the soluble TNFp75 receptor with other fragments encoding amino acids are well known to those of skill in the art. For example, DNA sequence encoding a fusion protein can be obtained by methods such as, restriction enzyme digestion, ligation or complementary cohesive ends.

The site-directed mutant DNA sequence encoding the mutant protein according to the present invention, obtained as stated above, is then inserted into a suitable expression vector and in turn transformed into a suitable host cell. Finally, the transformed host cell is cultured and the fusion protein is obtained by separation and purification.

Expression vectors useful in the present invention can be selected from a wide range, such as commercial vectors. For example, a commercial vector is selected, and the nucleotide sequence encoding the mutant protein according to the present invention is operably linked to an expression-regulating sequence, thereby creating a protein expression vector.

"Operably linked to" as used in the context of the present invention means such a situation that some parts of a linear DNA sequence may affect the activity of the other parts of the same DNA sequence. For example, if the signal peptide DNA participates peptide secretion as a precursor, it (the leader sequence for secretion) is "operably linked to" the polypeptide-encoding DNA; if a promoter controls transcription of a DNA sequence, it is "operably linked to" the encoding sequence; and if a ribosomal binding site is at a position that allows its translation, it is "operably linked to" the encoding sequence. Generally, "operably linked to" means neighboring; however, for the leader sequence for secretion, it means neighboring in the reading frame.

"Host cells" as used in the context of the present invention include eukaryotic cells and prokaryotic cells. Prokaryotic cells commonly used include *E. coli* and *Bacillus subtilis*, etc. Eukaryotic cells commonly used include yeast cells, insect cells and mammalian cells.

In an example of the invention, the method for preparing the soluble TNFRp75: Fc fusion protein comprises the steps of:

i. Modifying the sequence encoding the wild-type soluble TNFp75 receptor to replace the amino acid at position 92 and conjugating the modified sequence with a sequence encoding the Fc fragment, thereby obtaining a gene encoding the fusion protein;

ii. cloning the gene encoding the modified soluble TNFp75 receptor: Fc fusion protein obtained above into an expression plasmid;

iii. transforming a host cell with the expression plasmid caning the gene encoding the modified soluble TNFp75 receptor: Fc fusion protein;

iv. culturing the transformed host cell;

v. collecting the host cell and the culture medium, then separating and purifying the soluble TNFp75 receptor: Fc fusion protein.

The soluble TNFp75:Fc fusion protein in the present invention is useful in the treatment of diseases associated with TNF over-expression, including but not limited to, rheumatoid arthritis, psoriasis, scleroderma, Sjogren's syndrome, ankylosing spondylitis, lupus erythematosus, dermatomyositis, systemic lupus erythematosus-like syndrome, and so on.

Said soluble TNFp75:Fc fusion protein in the present invention can be used alone or in combination with other drugs such as chemotherapy drugs.

The present invention further provides a pharmaceutical composition comprising an effective amount of one or more soluble TNFp75:Fc fusion protein of the present invention, and at least one pharmaceutically acceptable carrier, diluent or excipient. In general, the above compositions may be prepared by mixing the active ingredient and the excipient, by diluting the active ingredient with the excipient, or by encapsulating the active ingredient in a carrier in the form of, for example, capsule or sachet. The diluent can be solid, semisolid, or liquid. The composition may be in the form of tablets, pills, powders, solutions, syrups and sterile injection solutions. Suitable examples of excipients may comprise one or more agents selected from the group consisting of lactose, glucose, sucrose, sorbitol, mannitol, starch, microcrystalline cellulose, polyvinylpyrrolidone, cellulose, water, etc. Such compositions may also contain one or more agents selected from the group consisting of diluents, emulsifiers, preserving agents (such as methyl hydroxybenzoate and propyl hydroxybenzoate), and sweetening agents.

Administration routes of the soluble TNFp75:Fc fusion protein and the pharmaceutical composition according to the present invention are not specifically limited and can be in a form suitable for oral administration, for parenteral injection, or for topical administration, such as intramuscular, intravenous, or subcutaneous injection, inhalation or spray. Oral administration is preferred.

When administered orally in the form of tablets or capsules, the soluble TNFp75:Fc fusion protein will normally be administered at a unit dose within the range of 1-1000 mg for an adult having average weight of 60-70 kg, or the soluble TNFp75:Fc fusion protein may be injected parenterally at a unit dose within the range of 0.1-500 mg. It can be administered once or several times per day. A unit dose of the pharmaceutical composition generally comprises the active ingredient within the range of 1-500 mg, typically 1 mg, 5 mg, 10 mg, 25 mg, 50 mg, 100 mg, 200 mg, 300 mg, 400 mg or 500 mg.

In the treatment of specific conditions, the dose and administration regime of the active ingredient according to the present invention will depend on various factors, including the body weight, age, gender, the symptom, the severity of the illness being treated, and the particular route and frequency of administration. Accordingly the optimum dosage could be determined by the practitioner who is treating any particular patient.

The wide-type soluble human TNFp75:Fc fusion protein employed in the present invention is obtained from AMGEN under the commercial name ENBREL. The TNFα employed in the present invention is obtained from R&D Company. $LT_{28-171}$ employed in the present invention is prepared according to the method disclosed in Chinese Application No. CN00111884.6.

The present invention is now illustrated with reference to examples. It should be understood that the examples are merely to illustrate the invention but not intended to limit the scope of the invention. Experiments in the following examples that do not indicate specific experimental conditions are performed under conventional conditions, for examples, those described in Sambrook, et al. *Molecular cloning: a laboratory manual* (New York: Cold Spring Harbor Laboratory Press, 1992), or under conditions suggested by manufacturers.

EXAMPLES

Example 1

Preparation of the TNFR75 (E92H): Fc Fusion Protein (1) Generation of the Gene Encoding the TNFRp75 (E92H):Fc Fusion Protein The mutant DNA sequence encoding the soluble TNF p75 receptor was obtained by SOE-PCR (Splicing by Overlapping Extension PCR) technology using the nucleotide sequence encoding the wild-type human soluble TNFRp75: Fc fusion protein as template. The first half of the DNA fragment encoding the soluble TNF p75 receptor, which comprises the mutantation site, was amplified using the encoding DNA of the wild-type soluble TNFRp75: Fc fusion protein as template and the following primers:

```
                                     (SEQ ID NO. 16)
    INFRp75p□aagcttatggctcccgtcgccgtctggg (SEQ ID NO. 17)
    E92HpF1□TGCTTGAGCTGTGGCTCCCG
```

Then the second half of the DNA fragment encoding the soluble TNF p75 receptor, which comprises both the mutantation site and the Fc fragment, was amplified using the following primers:

```
                                     (SEQ ID NO. 18)
    Fcp□gaattcctatttacccggagacaggg (SEQ ID NO. 19)
    E92HpR1□CGGGAGCCACAGCTCAAGCAgtgGGGAA
```

Finally the DNA fragment encoding the TNFRp75 (E92H): Fc fusion protein was PCR amplified using the two PCR products obtained above (i.e., the first half and the second half of the DNA fragment) as template and primers TNFRp75 and Fcp.

(2) Construction of Expression Vectors

After verification by sequencing, the PCR product obtained as stated above were digested with HindIII and EcoRI, then inserted into the commercial expression vector pcDNA3 (Invitrogen). The digestion and ligation were performed following the manufacturer's instructions.

(3) Transfection

The expression vector encoding the soluble TNF p75: Fc fusion protein were transformed into *E. coli* DH5α. The positive clones were expanded in 500 ml LB culture flask, and then DNA were extracted and purified by the Ultrapure Plasmid DNA Purification Kit (Qiagen) following the manufacturer's instructions. The plasmid DNA obtained as stated above were transfected into CHO-K1 cells (Chinese hamster ovary cells, obtained from ATCC) using the lipofectamine kit from Invitrogen following the manufacturer's instructions.

(4) Screening Clones 24-48 hours after the transfection, the culture medium was exchanged to be a screening medium containing G418(Geneticin). The screening medium was exchanged every 3 to 4 days till formation of the cell clones. When the cell clones grown into a diameter of 1 to 2 mm, monoclones were transferred into a 24-well plate. After the cells reach a confluence of 50 to 70%, supernatant in each well was tested by the ELISA assay, and the clones with high expression of the TNFRp75 mutant: Fc fusion protein were selected for screening with drug. The expression level of the TNFRp75 mutant: Fc fusion protein in each clone was measured when concentration of the drug reaches at the maximum, and two monoclonal cell strains which have high expression level and good growth were selected for seed storage.

The ELISA assay was performed as follows:

The antibody (anti-human TNFRp75-specific monoclonal antibody, R&D Company) was diluted to 1 ug/ml in the coating buffer (CBS, pH9.6), applied on a 96-well plate (100 ul/well), and allowed standing overnight at 5□. The liquid in the well was removed and the well was washed with PBST 3 times. After drying, 400 ul/well blocking solution (1% BSA PBST) was added to the plate and incubated for 2 hrs at room temperature, and then washed with PBST 3 times and air dried. The standard sample (Amgen, commercial name ENBREL) was serially diluted in the diluting solution. The supernatant with the expressed protein was diluted to 1 ug/ml and added to duplicate wells of the 96-well plate (100 ul/well). The plate was incubated for 1 hr at 37□. After that, the liquid in the wells was removed and the wells were washed 3 times and dried. The enzyme-linked antibody (HRP-anti-human IgG Fc-specific antibody, PIERCE) was diluted in the diluting solution to a certain concentration (1:20000), added to the 96-well plate (100 ul/well) and incubated for 1 hr at 37□. The liquid in the wells was then removed and the wells were washed 5 times and dried. The prepared substrate mix solution was added to the 96-well plate (100 ul/well) and incubated for 10 mins at 37□. A stop solution (50 ul/well) was added to the wells to stop the reaction. The OD value was read out at 490 nm, and content of the protein in the sample was calculated according to the standard curve.

(5) Cell Culture $1 \times 10^5$/ml cells were amplified in a 500 ml culture flask at 37□ for 3-4 days. Passage: when cell density reaches $2 \times 10^5$/ml, the cells were transferred into 720 cm² roller bottles and cultured for 3-4 days. Passage: $4 \times 10^7$ cells were transferred in to 1445 cm² roller bottles and cultured for 6 days. Exchange of culture medium: when the cell culture reaches the platform, the culture medium was exchanged for serum free medium (SFM, Gibco Inc.). Recovery of the culture medium: 6 days after grown in SFM, the supernatant liquor was collected and purified by Protein □A affinity chromatography to afford 8.7 mg of the TNFRp75 (E92H): Fc fusion protein.

Examples 2-7

Generation of Other TNFRp75 Mutant: Fc Fusion Proteins

The common primers for generating the nucleotide sequence encoding TNFRp75 (E92A): Fc, TNFRp75 (E92N): Fc, TNFRp75 (E92S): Fc, TNFRp75 (E92N, W89Y):Fc, TNFRp75 (E92S, W89Y): Fc and TNFRp75 (E92N, W89F): Fc are shown below:

```
TNFRp75F:
aagcttatggctcccgtcgccgtctggg       (SEQ ID NO. 16)

Fcp:
gaattcctatttacccggagacaggg         (SEQ ID NO. 18)
```

The specific primers for generating the nucleotide sequence encoding TNFRp75 (E92A): Fc, TNFRp75 (E92N): Fc, TNFRp75 (E92S): Fc, TNFRp75 (E92Q): Fc□TNFRp75 (E92N, W89Y): Fc, TNFRp75 (E92S, W89Y): Fc and TNFRp75 (E92N, W89F): Fc were shown in the table below:

| Mutants | Specific primers |
|---|---|
| TNFRp75(E92A): Fc | E92ApF1(SEQ ID NO. 20): TGCTTGAGCTGTGGCTCCCG E92ApR1(SEQ ID NO. 21): CGGGAGCCACAGCTCAAGCAggcGGGAA |

-continued

| Mutants | Specific primers |
|---|---|
| TNFRp75(E92N): Fc | E92NpF1(SEQ ID NO. 22): TGCTTGAGCTGTGGCTCCCG<br>E92NpR1(SEQ ID NO. 23): CGGGAGCCACAGCTCAAGCAgttGGGAA |
| TNFRp75(E92S): Fc | E92SpF1(SEQ ID NO. 24): TGCTTGAGCTGTGGCTCCCG<br>E92SpR1(SEQ ID NO. 25): CGGGAGCCACAGCTCAAGCAgctGGGAA |
| TNFRp75(E92N, W89Y): Fc | E92NW89YpF1(SEQ ID NO. 26): GTTCCCGAGTGCTTGAG<br>E92NW89YpR1(SEQ ID NO. 27): CGGGAGCCACAGCTCAAGCAgttGGGAA CgtaGTTCCAGAGCTGGGTGTATGT |
| TNFRp75(E92S, W89Y): Fc | E92SW89YpF1(SEQ ID NO. 28): GTTCCCGAGTGCTTGAG<br>E92SW89YpR1(SEQ ID NO. 29): CGGGAGCCACAGCTCAAGCAgctGGGAA CgtaGTTCCAGAGCTGGGTGTATGT |
| TNFRp75(E92N, W89F): Fc | E92NW89FpF1(SEQ ID NO. 30): GTTCCCGAGTGCTTGAG<br>E92NW89FpR1(SEQ ID NO. 31): CGGGAGCCACAGCTCAAGCAgttGGGAA CgaaGTTCCAGAGCTGGGTGTATGT |

Other procedures were identical with that of Example 1.

Example 8

The Neutralizing Activity Assay of the TNFRp75 Mutant: Fc Fution Protein Against $LT_{28-171}$ (1) Cell Seeding L929 cells were seeded into a 96-well microtiter plate at a density of $1.0 \times 10^6$ cells/well. Actinomycin D, 1 ng/ml $LT_{28-171}$, and TNFRp75 (E92A):Fc of gradient concentrations were added into each cell of the experimental group, and Actinomycin D, 1 ng/ml $T_{28-171}$, and the wild-type rhTNFRp75:Fc of gradient concentrations were added into each cell of the control group. The 96-well plates were incubated at 37□, 5% $CO_2$ for 24 h.

(2) End-Point Measurement

The culture medium was completely removed from the 96-well plates. The dying solution of 40 ul was added into each well. After 10 minutes, the dying solution was removed and the plate was washed with water 3 times till the used water was colorless.

The residual water was allowed to be dried as far as possible. The decoloring solution of 100 ul/well was added into each well of the 96-well plates and mixed thoroughly. The plates were read out by an enzyme-labelled meter at 570 nm.

(3) Result Analysis:

The results were automatically analyzed by the Four Parameter Equation in the PraphPad Prism4.0 data-processing software: the x-axis is logarithm of the concentration of the standard sample, and the y-axis is the $OD_{570}$ value. The concentration for 50% of the maximum effect (EC50) was also provided by the software, which was 7.93 ng/ml for the neutralizing activity of TNFRp75 (E92A): Fc on LT, and 22.31 ng/ml for the neutralizing activity of the wild-type rhTNFRp75:Fc on LT. The neutralizing activity of the mutant against LT was increased by 291%. An "S" curve plotted according to the experimental results was shown in FIG. 1.

The neutralizing activity assay of other TNFRp75: Fc mutants against the cytotoxicity of $LT_{28-171}$ was carried out in the same manner. The results were shown in the table below. An "S" curve plotted according to the experimental results was shown in FIG. 2-6.

| Mutants | EC50(ng/ml) of the neutralizing activity of the wild-type TNFRp75: Fc against LT/EC50(ng/ml) of the neutralizing activity of the mutants against LT | Enhancement of the neutralizing activity against LT (□) |
|---|---|---|
| TNFRp75(E92A): Fc | 23.11/7.93 | 291% |
| TNFRp75(E92H): Fc | 44.05/3.74 | 1177% |
| TNFRp75(E92N): Fc | 21.99/7.94 | 277% |
| TNFRp75(E92N, W89Y): Fc | 54.49/3.74 | 1457% |
| TNFRp75(E92S, W89Y): Fc | 23.11/6.28 | 368% |
| TNFRp75(E92N, W89F): Fc | 23.28/7.56 | 308% |

Example 9

The Neutralizing Activity Assay of the TNFRp75: Fc Mutant Against the Cytotoxicity of TNFα

L929 cells were seeded into a 96-well microtiter plate at a density of $1.0 \times 10^6$ cells/well. Actinomycin D, 10 ng/ml TNFα, and TNFRp75:Fc or the mutants thereof in gradient concentrations were added into each cell of the plate. The 96-well plate was incubated at 37□, 5% $CO_2$ for 24 h.

Other procedures and data-processing are performed as those described for Example 8.

The results were shown in the table below. X-axis in the figure is logarithm of concentration (ng/ml) of the fusion protein, and the y-axis is the light absorption at 570 nm.

| Mutants | EC50(ng/ml) of the neutralizing activity of the wild-type TNFRp75: Fc against LT/EC50(ng/ml) of the neutralizing activity of the mutants against LT | Enhancement of the neutralizing activity against TNFα (□) |
|---|---|---|
| TNFRp75(E92A): Fc | 8.25/6.34 | 130% |
| TNFRp75(E92H): Fc | 11.63/9.03 | 129% |
| TNFRp75(E92N): Fc | 7.43/5.68 | 131% |
| TNFRp75(E92N, W89Y): Fc | 7.52/5.04 | 149% |
| TNFRp75(E92S, W89Y): Fc | 16.29/12.22 | 133% |
| TNFRp75(E92N, W89F): Fc | 13.06/1020 | 128% |

An "S" curve was plotted according to the experimental results using the GraphPad Prism4.0 software, as shown in FIG. 1-6.

Example 10

Measurement of the Binding Constant of TNFRp75 (E92N☐W89Y):Fc for TNFα and LT (1) Materials and Instruments:

A. The ligands TNF-α and LT, the receptors rhTNFRp75: Fc, and TNFRp75 (E92N, W89Y):Fc 3.8 mg/mL B. HBS-P buffer (10 mM HEPES, 150 mM NaCl, 3 mM EDTA, 0.005% (v/v) surfactant P20, pH 7.4).

C. The activating agent N-ethyl-N'-dimethylaminopropyl carbodiimide (EDC), N-hydroxysuccinimide (NHS), ethanolamine, etc., all purchased from Sigma company.

D. Instruments for measuring interaction between biological macromolecules: BIAcore3000, carboxymethylcellulose sensor chip (CM5) (G.E. Inc.) purchased from GE company.

(2) Methods

A. Conjugation of rhTNFRp75: Fc

The rhTNFRp75: Fc was conjugated to the FC2 channel of the CM5 chip using the amino conjugation method provided in the software Wizard of Biacore3000. HBS-P was used as a running buffer, and 1 mg/mL of rhTNFRp75: Fc was diluted to a final concentration of 100 μg/mL in a NaAC solution (10 mM, pH4.0). EDC (0.2M) and NHS (50 mM) were mixed in a ratio of 1:1, and then applied onto the surface of the chip at a flow rate of 10 μL/min for 7 mins. Thereafter, solution of the receptor was applied and then ethanolamine (1M, pH8.5) was applied to block the activated surface of the chip. The final conjugation amount of the TNFRp75 was 7043.6 RU.

B. Conjugation of TNFRp75 (E92N, W89Y): Fc

The TNFRp75 (E92N, W89Y): Fc was conjugated to the FC4 channel of the CM5 chip using the amino conjugation method provided in the software Wizard of Biacore3000. HBS-P was used as a running buffer, and 3.8 mg/mL of TNFRp75 (E92N, W89Y): Fc was diluted to a final concentration of 100 μg/mL in a NaAC solution (10 mM, pH4.0). EDC (0.2M) and NHS (50 mM) were mixed in a ratio of 1:1, and then applied onto the chip surface at a flow rate of 10 μL/min for 7 mins. Thereafter, solution of the receptor was applied and then ethanolamine (1M, pH8.5) was applied to block the activated surface of the chip. The final conjugation amount of the TNFRp75 (E92N, W89Y): Fc was 6275.0 RU.

C. Primary Screening and Kinetics Assay of rhTNFRp75: Fc

The binding activity of the receptor TNFRp75: Fc to TNF or LT was measured by SPR (surface plasma resonance). The ligands were diluted in the HBS-P buffer to a concentration of 1 nm or 10 nm, respectively, and then centrifuged and injected automatically to measure the binding activity of the receptor TNFRp75 to ligands of various concentrations. Ligands showing binding activity were subjected to kinetics assay.

The stock solution of TNFα in a concentration of 10 μg/L (575 nM) was serially diluted into 0, 0.3125, 0.625, 1.25, 2.5, 5.0, 10.0, and 20.0 nM in the HBS-P buffer.

The stock solution of LT in a concentration of 2.25 mg/mL (137 μM) was serially diluted into 0, 0.3125, 0.625, 1.25, 2.5, 5.0, 10.0, and 20.0 nM in the HBS-P buffer.

The interaction of the receptor and the ligand was measured in kinetics assay using Wizard of Biacore3000. All the ligands were applied at a flow rate of 40 μL/min for 1 min, dissociated for 2 min, and then 50 mM NaOH and HBS-P buffer were applied at a flow rate of 100 pL/min for 15 s and 60 s to regenerate the ligands (50 mM NaOH and HBS-P buffer were applied at a flow rate of 100 μL/min for 10 s and 30 s to regenerate in the primary screening). The experimental data were fit to the 1:1 Langmuir association model in the analysis software of Biacore3000 to provide the specific kinetic constant.

D. Primary Screening and Kinetics Assay of TNFRp75 (E92N, W89Y): Fc

The binding activity of the receptor TNFRp75(E92N, W89Y): Fc to TNF or LT was measured by SPR (surface plasma resonance). The ligands were diluted in the HBS-P buffer to a concentration of 1 nm or 10 nm, respectively, and then centrifuged and injected automatically to measure the binding activity of the receptor TNFRp75(E92N, W89Y): Fc to ligands of various concentrations. Ligands showing binding activity were subjected to kinetics assay.

The stock solution of TNFα in a concentration of 10 μg/mL (575 nM) was serially diluted into 0, 0.3125, 0.625, 1.25, 2.5, 5.0, 10.0, and 20.0 nM in the HBS-P buffer.

The stock solution of LT in a concentration of 2.25 mg/mL (137 μM) was serially diluted into 0, 0.3125, 0.625, L25, 2.5, 5.0, 10.0, and 20.0 nM in the HBS-P buffer.

The interaction of the receptor and the ligand was measured in kinetics assay using Wizard of Biacore3000. All the ligands were applied at a flow rate of 40 μL/min for 1 min, dissociated for 2 min, and then 50 mM NaOH and HBS-P buffer were applied at a flow rate of 100 μL/min for 15 s and 60 s to regenerate the ligands (50 mM NaOH and HBS-P buffer were applied at a flow rate of 100 μL/min for 10 s and 30 s to regenerate in the primary screening). The experimental data were fit to the 1:1 Langmuir association model in the analysis software of Biacore3000 to provide the specific kinetic constant.

(3) Results:

A. The binding kinetics data of rhTNFRp75: Fc for TNFα (abbreviated as TNF) and LT were shown below.

| Ligands | $K_a$(1/Ms) | $K_d$(1/s) | $K_D$(nM) | Chi$^2$ |
|---|---|---|---|---|
| TNF | $8.45 \times 10^3$ | $4.1 \times 10^{-6}$ | $4.85 \times 10^{-10}$ | 107 |
| LT | $5.23 \times 10^3$ | $6.99 \times 10^{-7}$ | $1.34 \times 10^{-10}$ | 8.86 |

B. The binding kinetics data of TNFRp75 (E92N, W89Y): Fc for TNFα (abbreviated as TNF) and LT were shown below.

| Ligands | $K_a$(1/Ms) | $K_d$(1/s) | $K_D$(nM) | Chi$^2$ |
|---|---|---|---|---|
| TNF | $9.72 \times 10^3$ | $1.29 \times 10^{-6}$ | $1.33 \times 10^{-10}$ | 26.6 |
| LT | $1.88 \times 10^4$ | $1.64 \times 10^{-6}$ | $8.74 \times 10^{-11}$ | 2.04 |

Compared with TNFRp75: Fc, the equilibrium dissociation constant (KD) of TNFRp75 (E92N, W89Y) for TNFα or LT showed a 2- to 3-fold decrease, indicating that the binding affinity of TNFRp75 (E92N, W89Y) to TNFα or LT was enhanced. In addition, the dissociation constant ($k_d$) of TNFRp75 (E92N, W89Y) for TNFα was remarkably lower than that of TNFRp75: Fc, indicating that the complex of TNFRp75 (E92N, W89Y) and TNFα is more stable in vitro, which may improve the half-life of TNFRp75 (E92N, W89Y) in vivo.

The specific embodiment described above are merely to illustrate the invention but not intended to restrict the scope of the invention. The present invention will also encompass the functionally equivalent methods and components. In light of the description herein as well as the accompanying drawings, those of skill in the art can readily make various changes and modifications, which will also fall into the scope of the invention.

The invention claimed is:

1. A soluble TNFRp75 mutant comprising N-terminal 257 amino acid residues of TNFRp75, the amino acid sequence of TNFRp75 being set forth in SEQ ID NO. 1, wherein an N-terminal residue Glu92 of the amino acid sequence set forth in SEQ ID NO. 1 is substituted in the mutant.

2. The soluble TNFRp75 mutant of claim 1, wherein the N-terminal residue Glu92 of the amino acid sequence set forth in SEQ ID NO. 1 is substituted by one of Asn, His, Ser, Ala, Lys or Gln.

3. The soluble TNFRp75 mutant of claim 1, wherein the N-terminal residue Trp89 of the amino acid sequence set forth in SEQ ID NO. 1 is substituted in the mutant.

4. The soluble TNFRp75 mutant of claim 3, wherein the N-terminal residue Glu92 of the amino acid sequence set forth in SEQ ID NO. 1 is substituted by one of Asn, His, Ser, Ala, Lys or Gln; and in addition, the N-terminal residue Trp89 of the amino acid sequence set forth in SEQ ID NO. 1 is substituted by one of Tyr, Phe, His, Lys, Met, and Leu.

5. A fusion protein formed between the soluble TNFRp75 mutant of claim 1 and human immunoglobulin constant region, wherein the immunoglobulin constant region is at the C-terminus of the soluble TNFRp75 mutant.

6. The fusion protein of claim 5, wherein said additional amino acid fragment is the 232 amino acid residues of human immunoglobulin constant region.

7. A DNA sequence encoding a soluble TNFRp75 mutant wherein the soluble TNFRp75 mutant comprises the N-terminal 257 amino acid residues of TNFRp75, the amino acid sequence of TNFRp75 being set forth in SEQ ID NO. 1, wherein the N-terminal residue Glu92 of the amino acid sequence set forth in SEQ ID NO. 1 is substituted in the mutant.

8. A DNA sequence encoding a soluble TNFRp75 mutant-human Ig constant region fusion protein, wherein the DNA sequence comprises the DNA sequence of claim 7 and a DNA sequence encoding a human immunoglobulin constant region, wherein the immunoglobulin constant region is at the C-terminus of the soluble TNFRp75 mutant.

9. A method for treating rheumatoid arthritis, psoriasis, scleroderma, ankylosing spondylitis, or dermatomyositis, wherein the method comprises administering to a subject in need thereof a therapeutically effective amount of the soluble TNFRp75 mutant of claim 1.

10. A pharmaceutical composition comprising a therapeutically effective amount of the soluble TNFRp75 mutant of claim 1 and a pharmaceutically acceptable carrier.

11. A method for treating rheumatoid arthritis, psoriasis, scleroderma, ankylosing spondylitis, or dermatomyositis, wherein the method comprises administering to a subject in need thereof a therapeutically effective amount of the fusion protein of claim 5.

12. A pharmaceutical composition comprising a therapeutically effective amount of the fusion protein of claim 5 and a pharmaceutically acceptable carrier.

13. A fusion protein formed between the soluble TNFRp75 mutant of claim 2 and human immunoglobulin constant region, wherein the immunoglobulin constant region is at the C-terminus of the soluble TNFRp75 mutant.

14. A fusion protein formed between the soluble TNFRp75 mutant of claim 3 and human immunoglobulin constant region, wherein the immunoglobulin constant region is at the C-terminus of the soluble TNFRp75 mutant.

15. A fusion protein formed between the soluble TNFRp75 mutant of claim 4 and human immunoglobulin constant region, wherein the immunoglobulin constant region is at the C-terminus of the soluble TNFRp75 mutant.

16. The DNA sequence of claim 7 wherein the N-terminal residue Glu92 of the amino acid sequence set forth in SEQ ID NO. 1 is substituted by one of Asn, His, Ser, Ala, Lys or Gln.

17. A method for treating rheumatoid arthritis, psoriasis, scleroderma, ankylosing spondylitis, or dermatomyositis, wherein the method comprises administering to a subject in need thereof a therapeutically effective amount of the soluble TNFRp75 mutant of claim 2.

18. A pharmaceutical composition comprising a therapeutically effective amount of the soluble TNFRp75 mutant of claim 2 and a pharmaceutically acceptable carrier.

19. A method for treating rheumatoid arthritis, psoriasis, scleroderma, ankylosing spondylitis, or dermatomyositis, wherein the method comprises administering to a subject in need thereof a therapeutically effective amount of the fusion protein of claim 6.

20. A method for treating rheumatoid arthritis, psoriasis, scleroderma, ankylosing spondylitis, or dermatomyositis, wherein the method comprises administering to a subject in need thereof a therapeutically effective amount of the soluble TNFRp75 mutant of claim 3.

\* \* \* \* \*